US010670592B2

(12) United States Patent
Huo et al.

(10) Patent No.: US 10,670,592 B2
(45) Date of Patent: Jun. 2, 2020

(54) DETECTION OF ANALYTES USING METAL NANOPARTICLE PROBES AND DYNAMIC LIGHT SCATTERING

(71) Applicant: UNIVERSITY OF CENTRAL FLORIDA RESEARCH FOUNDATION, INC., Orlando, FL (US)

(72) Inventors: Qun Huo, Orlando, FL (US); Xiong Liu, Oviedo, FL (US); Qiu Dai, San Jose, CA (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 16/244,628

(22) Filed: Jan. 10, 2019

(65) Prior Publication Data
US 2019/0204313 A1    Jul. 4, 2019

Related U.S. Application Data

(62) Division of application No. 14/537,324, filed on Nov. 10, 2014, now Pat. No. 10,191,041, which is a division of application No. 12/810,876, filed as application No. PCT/US2009/030087 on Jan. 5, 2009, now Pat. No. 8,883,094.

(Continued)

(51) Int. Cl.
| | |
|---|---|
| *G01N 33/543* | (2006.01) |
| *G01N 15/02* | (2006.01) |
| *C12Q 1/682* | (2018.01) |
| *G01N 33/542* | (2006.01) |
| *G01N 33/58* | (2006.01) |

(Continued)

(52) U.S. Cl.
CPC ....... *G01N 33/54346* (2013.01); *C12Q 1/682* (2013.01); *G01N 15/0205* (2013.01); *G01N 33/542* (2013.01); *G01N 33/585* (2013.01); *C40B 60/12* (2013.01); *G01J 3/4412* (2013.01)

(58) Field of Classification Search
CPC ........ C12Q 1/682; C40B 60/12; G01J 3/4412; G01N 15/0205; G01N 33/542; G01N 33/54346; G01N 33/585
See application file for complete search history.

(56) References Cited

U.S. PATENT DOCUMENTS

| | | | |
|---|---|---|---|
| 4,762,413 | A | 8/1988 | Namba et al. |
| 4,975,237 | A | 12/1990 | Watling |

(Continued)

FOREIGN PATENT DOCUMENTS

| | | |
|---|---|---|
| WO | 199413835 | 6/1994 |

OTHER PUBLICATIONS

Huo, Q. et al, "A One-Step Homogeneous Immunoassay for Cancer Biomarker Detection Using Gold Nanoparticle Probes Coupled with Dynamic Light Scattering", J. Am. Chem. Soc., 2008, vol. 130, pp. 2780-2782.

(Continued)

*Primary Examiner* — Jeremy C Flinders
(74) *Attorney, Agent, or Firm* — Timothy H. Van Dyke; Beusse, Wolter, Sanks & Maire PLLC

(57) ABSTRACT

Disclosed herein are systems and methods for detecting Chemical Species, Biomolecules and Biotargets (Analytes) using receptor functionalized metal nanoparticles and Dynamic Light Scattering.

4 Claims, 10 Drawing Sheets

Specification includes a Sequence Listing.

A: An embodiment with two different metal nanoparticle probes

B: An embodiment with one type of metal nanoparticle probes

C: An embodiment with one type of metal nanoparticle probes, plus a nanoparticle aggregate inducer

Related U.S. Application Data

(60) Provisional application No. 61/018,719, filed on Jan. 3, 2008, provisional application No. 61/034,334, filed on Mar. 6, 2008.

(51) Int. Cl.
*G01J 3/44* (2006.01)
*C40B 60/12* (2006.01)

(56) References Cited

U.S. PATENT DOCUMENTS

| | | | |
|---|---|---|---|
| 5,104,621 | A | 4/1992 | Pfost et al. |
| 5,730,938 | A | 3/1998 | Carbonari et al. |
| 6,618,144 | B1 | 9/2003 | Reed |
| 2002/0103517 | A1 | 8/2002 | West et al. |
| 2003/0142309 | A1 | 7/2003 | Kuebler et al. |
| 2005/0112784 | A1 | 5/2005 | Yguerabide et al. |
| 2005/0130167 | A1 | 6/2005 | Bao et al. |
| 2007/0275415 | A1 | 11/2007 | Srinivasan et al. |
| 2009/0246142 | A1* | 10/2009 | Bhatia ............... A61K 49/1833 514/1.1 |

OTHER PUBLICATIONS

Huo Q., et al. "A One-Step Highly Sensitive Method for DNA Detection Using Dynamic Light Scattering", J. Am. Chem. Soc., 2008, vol. 130, pp. 8138-8139.

Turkevitch, J. et al., "A Study of the Nucleation and Growth Processes in the Synthesis of Colloidal Gold", Discuss, Faraday Soc., 1951, vol. 11, p. 55-75.

Frenz, G., "Controlled Nucleation for the Regulation of the Particle Size in Monodisperse Gold Suspension", Nature Phys. Sci., 973, vol. 241, p. 20-22.

Elghanian, R. et al., "Selective Colorimetric Detection of Polynucleotides Based on the Distance-Dependent Optical Properties of Gold Nanoparticles", Science, 1997, vol. 277, pp. 1078-1081.

Taton, T. A. et al., "Scanometric DNA Array Detection with Nanoparticle Probes", Science, 2000, vol. 289, pp. 1757-1760.

Cao, Y. W. et al., "Nanoparticles with Raman Spectroscopic Fingerprints for DNA and RNA Detection", Science, 2002, vol. 297, pp. 1536-1540.

Jin, R. et al., "What Controls the Melting Properties of DNA-Linked Gold Nanoparticle Assemblies?", J. Am. Chem. Soc., 2003, vol. 125, pp. 1643-1654.

Stoeva, S. I. et al., "Multiplexed DNA Detection with Biobarcoded Nanoparticle Probes", Chem. Int. Ed., 2006, vol. 45, pp. 3303-3306.

Cobbe, Stephen et al., "DNA-Controlled Assembly of Protein-Modified God Nanocrystals", J. Phys. Chem, B., 2003, vol. 107, pp. 470-477.

Storhoff JJ et al., "What controls the optical properties of DNA-linked gold nanoparticle assemblies?", Journal of the American Chemical Society vol. 122, No. 19, May 17, 2000, pp. 4640-4650.

Sang Jun Sim et al., Signal enhancement of surface Plasmon resonance immunoassay using enzyme precipitation-functionalized gold nanoparticles: A femto molar level measurement of anti-glutamic acid decarboxylase antibody, Biosensors & Bioelectronics Elsevier UK, vol. 22, No. 9-10, Apr. 15, 2007, pp. 1874-1880.

Liu Xiong et al., A one-step homogeneous immunoassay for cancer biomarker detection using gold nanoparticle probes coupled with dynamic light scattering. Journal of the American Chemical Society, vol. 130, No. 9, Mar. 5, 2008, pp. 2780-2782.

Lant et al., Applied Optics, 1997, vol. 36, pp. 7501-7507.

\* cited by examiner

A: An embodiment with two different metal nanoparticle probes

B: An embodiment with one type of metal nanoparticle probes

C: An embodiment with one type of metal nanoparticle probes, plus a nanoparticle aggregate inducer DNA1: 5'TAA CAA TCC CTC-C3-SS 3'
DNA2: 5'SS-C6-ATC CTT ATC AAT ATT 3'
Target DNA: 5'GAG GGA TTA TTG TTA AAT ATT GAT AAG GAT 3'

DETECTION OF ANALYTES USING METAL NANOPARTICLE PROBES AND DYNAMIC LIGHT SCATTERING

CROSS REFERENCE TO RELATED APPLICATIONS

The present application is a divisional of U.S. Ser. No. 14/537,324 filed on Nov. 10, 2014, which is a divisional of U.S. Ser. No. 12/810,876 filed on Jun. 28, 2010, which is a 371 of PCT/US09/030087 filed Jan. 5, 2009, which claims priority to U.S. Provisional Application 61/018,719 filed Jan. 3, 2008 and U.S. Provisional Application 61/034,334 filed Mar. 6, 2008. Priority under 35 USC 119 is claimed and the applications are incorporated herein by reference.

STATEMENT REGARDING FEDERALLY SPONSORED RESEARCH OR DEVELOPMENT

This invention was made with Government support under agency contract/grant nos. 0552295 and 0506531 awarded by the National Science Foundation. The Government has certain rights in this invention.

FIELD OF THE INVENTION

The present invention relates to systems and methods for detecting Chemical Species, Biomolecules and Biotargets (all termed as Analytes) using receptor functionalized metal nanoparticles. Receptor is a general term for any chemical species and biomolecules that can interact with the analyte through covalent or non-covalent chemical interactions.

BACKGROUND

There is a need to detect various Chemical Species, Biomolecules and Biotargets for a variety of purposes, such as medical diagnosis, human and animal health monitoring, life science research, drug screening and pharmaceutical development, environmental protection, industrial process monitoring, food safety monitoring, detection of illegal drug usage, homeland security, monitoring of other chemical and biological process.

BRIEF DESCRIPTION OF THE DRAWINGS

FIG. 3(b) is a partial side view of the system shown in FIG. 3(a). Note: (1) The sample platform can be movable or fixed. The platform shown comprises 12 fixed assay solution containers (in this case, 12 microwells), or removable containers to hold the assay solutions. (3) When it can be rotated, samples may be continuously added and removed from the carousel using removable assay solution containers as shown in FIG. 3(c). This mode can be set for continuous measurement of multiple samples at a preset time interval. (4) The relative angle between incident light beam and scattered light beam that will be detected by the detector is typically an angle between 0-90 degree. Illustrated here the angle is approximately 13-25 degree. (5) The carousel may be replaced by a microfluidic device which can be placed and removed from the carousel. (6) The number of sample holders and detectors can be 1 or any other number.

DETAILED DESCRIPTION

Embodiments of the invention pertain to a highly sensitive, fast and convenient homogeneous one-step analytical assay for monitoring and detecting Chemical Species, Biomolecules and Biotargets (all termed as analyte) including but not limited to, proteins, antibodies, antigens, enzymes, nucleic acids, hormones, drugs, drug intermediates, environmental polluting chemicals and species, chemical and biological warfare agents, bacteria and viruses, synthetic chemical substances.

Figure 1:
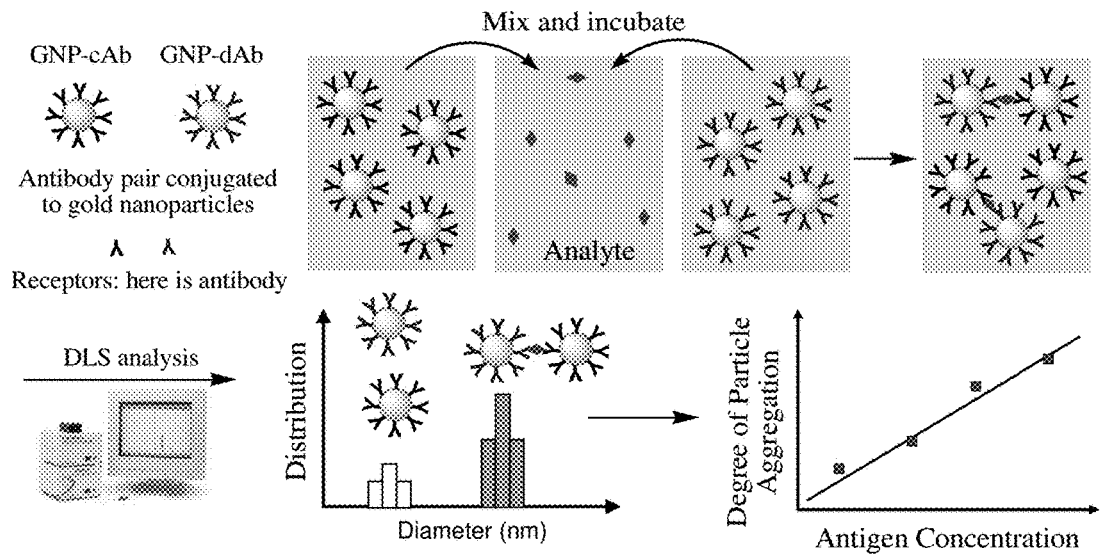
FIG. 1 is a schematic illustration of the invention including three different embodiments. The illustration is an example based on a homogeneous immunoassay using gold nanoparticles (GNP) coupled with dynamic light scattering (DLS) measurement. In embodiment A, two different probes are used. The probes are gold nanoparticles conjugated with a matched antibody pair. In embodiment B, a single type of probe is used. The analyte contains multiple binding sites with the probe, therefore, can cause nanoparticle aggregation upon binding with the receptors on the probes. In embodiment C, a single type of probe is used. However, the binding between analyte and probes does not cause particle aggregation. Instead, an aggregation inducer is present to introduce nanoparticle aggregation. The analyte and aggregation inducer compete with each other to bind with the probes.
Figure 1:
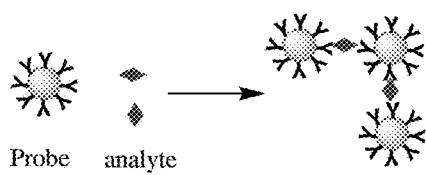
Figure 1:
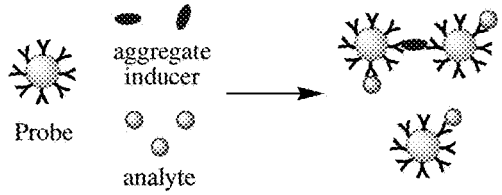

In a general embodiment, the invention pertains to an analytical method for the detection of analyte comprises the steps of providing a plurality of probes each comprising a metal nanoparticle conjugated with multiple copies of the same or different receptors. FIG. 1 is a general illustration of the invention. The illustration is an example based on a homogeneous immunoassay using gold nanoparticles (GNP) coupled with dynamic light scattering (DLS) measurement. The receptor can be a natural receptor (e.g. antibody, protein, DNA, etc.) or a synthetic receptor (e.g. molecules, ions, polymers or other chemical species). A sample solution suspected of including at least one analyte is contacted with the probes to form an assay solution, wherein in a presence of the analyte a portion of the probes in the analyte comprising solution become aggregated. Dynamic light scattering (DLS) is used to quantify the analyte by measuring the degree of aggregation of the assay solution. At least a presence of, and generally also the concentration of, the analyte in the sample solution is determined from DLS data obtained from the assay solution as determined by DLS. The concentration of the analyte determined can be used to base a medical diagnosis or prompt further tests to base a diagnosis, such as whether an individual has (or is likely to have) cancer, or other purposes such as environmental monitoring.

In another embodiment (the embodiment B as illustrated in FIG. 1), referred to herein as a single probe type embodiment, a first probe is the only probe type provided. This probe contains multiple copies of a single type or mixed types of receptors on one nanoparticle. In this embodiment the analyte can have multiple binding sites and the same probe type can bind to the multiple sites of the analyte to create nanoprobe aggregates. By way of example only, the nanoparticles may be conjugated with a layer of multiple polyclonal antibody which can bind with different epitopes of an antigen. Such binding will cause probe aggregation which is detectable by DLS. Another example is a nanoparticle probe with a layer of metal ion-binding ligands attached to the surface. The probe can form a coordination complex with the metal ion through ligands attached to the probe. When the probe is contacted with a sample that contains the metal ion as analyte, nanoparticle probe aggregation will occur due to complex formation, which can be detected by DLS.

In another embodiment (the embodiment A as illustrated in FIG. 1), referred to herein as the multiple probe type embodiment, the method includes both a plurality of first probes and a plurality of second probes, wherein the second probes comprise a metal nanoparticle conjugated with a second receptor that is different from the first receptor. The first and second metal nanoparticles can be the same or different. In this embodiment the first and second receptor can both be selected to bind with the analyte and generally recognize separate sites on the analyte to bind. In this way, the respective receptors do not generally inhibit the other receptor's binding.

In the case of receptors comprising antibodies regarding an antigen target, the antibody combination should be qualified as "matched pairs", meaning that they can recognize separate epitopes on the antigen so they do not significantly hinder each other's binding. In this particular case, the first and second receptors may be referred to herein as in ELISA as the "capture antibody" and the "detection antibody". However, the present invention has little relation to ELISA. ELISA is a heterogeneous multiple step immunoassay. Embodiments of the present invention provide a homogenous assay that removes the ELISA need for binding the capture antibody to a solid phase typically attached to the bottom of a plate well, adding antigen and allowing complexation with the bound antibody, washing to obtain unbound product, and a second binding step where the detection antibody is allowed to bind to the antigen. Another difference is the use of Dynamic light scattering (DLS) to quantify the analyte, as compared to ELISA which achieves quantitation by measuring the amount of labeled second antibody bound to the matrix through the use of an enzymatic probes, fluorescent probes, or radioactive probes.

In a third embodiment (the embodiment C as illustrated in FIG. 1), the method involves the use of plurality of a single probe with multiple copies of receptors conjugated to the nanoparticle surface. The probe will mainly bind to one site of the analyte. The probe particles can form aggregates by a molecule or material different from the analyte. This molecule or material can be called as "aggregation inducer". This molecule or material can be another chemical species, a different nanoparticle, or a material that is co-existed with analyte in the sample solution, or that is added to the sample solution from sources other than the sample solution. The aggregation inducer competes with analyte to bind with the probe. The binding between probes and analyte will inhibit the probe aggregation caused by aggregation inducer. When the probes are contacted with the sample solution, the probes will form aggregate introduced by the aggregation inducer molecule. The analyte will not cause or cause much less aggregation of nanoparticle probes than the aggregation inducers. Therefore, if there is analyte in the sample solution, there will be less degree of probe aggregation. The degree of probe aggregation is inversely proportional to the analyte concentration. An example for this embodiment is a competitive immunoassay that utilizes a probe containing a single type of primary antibody on the nanoparticle surface. This probe may be aggregated together by mixing with a secondary antibody solution. In this case, the secondary antibody is the aggregation inducer. For example, if the probe contains a primary antibody raised from mouse, a goat anti-mouse IgG may be used as an aggregation inducer. When the probe solution is mixed with sample solution that contains the antigen, the antigen molecule will compete with the secondary antibody to bind with the probe. Because the antigen-probe binding will not cause probe aggregation. As a result, when antigen is present in the sample, less degree of probe aggregation will occur compared to when antigen is absent from the sample. The antigen concentration in the sample solution can be quantified by DLS measurement and is inversely proportional to the degree of nanoparticle aggregation.

Quantitation according to embodiments of the present invention comprises directing light (e.g. ultraviolet, visible, near infrared or infrared) toward the analyte comprising solution mixed with plurality of nanoparticle probes, and measuring a scattered light signal from the assay solution. At least a presence of, and generally also the concentration of, the analyte in the sample solution is determined from using dynamic light scattering to obtain DLS data from the assay solution. DLS data includes but is not limited to particle size, and/or particle size distribution and/or diffusion coefficient of particles in the assay solution. The concentration of the analyte determined can be used for multiple purposes as described herein, e.g., to base a medical diagnosis or prompt further tests to base a diagnosis, such as whether an individual has (or is likely to have) cancer.

The nanoparticles are generally metals, such as gold or silver which are both known to provide large scattering cross sections (Yguerabide, J.; Yguerabide, E. E. *Anal. Biochem.* 1998, 262, 137). The nanoparticles can have different shapes and chemical compositions such as spherical nanoparticles, nanorods, nanoshells, alloyed nanoparticles (nanoparticles with more than one metal components), nanocages, nanorice, etc. Other nanoparticles or colloidal particles that provide large scattering cross sections may be useful as well. The present invention is generally described herein with respect to gold nanoparticles. For example, gold nanoparticles, including spherical particles, nanorods or nanoshells with a size ranging from 10s to 100s nanometers, provide exceptionally large light scattering cross sections in the surface plasmon resonance wavelength region. The magnitude of light scattering by a gold nanoparticle is orders of magnitude higher than light emission from strongly fluorescing dyes such as fluorescein. This strong light scattering property of gold nanoparticles has been applied to optical microscopic imaging of biological cells for qualitative evaluation, but not for quantitative analysis and assays in homogeneous solutions by dynamic light scattering method. The strong light scattering makes gold and silver nanoparticles as excellent optical probe/tracer for analytical applications.

Receptors can be any moiety known to associate to a given target analyte. In competitive assay embodiment, receptor will also bind to the aggregation inducers. Analytes and aggregation inducers compete to bind with the receptor.

The receptors are adapted for binding to an analyte. Receptors can include, but are not limited to, antibody, DNAs, RNAs, proteins including enzymes, cells or cell components, biomimetics, synthetic molecules or materials which can specifically bind to the analyte. Biomimetic receptors can include molecular imprint antibodies, DNA-based aptamers, and peptide nucleic acids (PNA).

The receptor molecules (natural and synthetic) will be attached to the metal nanoparticles through covalent or non-covalent chemical interactions to prepare the probe. Methods for attachment of bioreceptor molecules such as antibody to gold nanoparticles through non-covalent chemical interactions have been well known and commonly practiced. For covalent attachment, the nanoparticles should have at least one chemical functional group such as carboxylic acid or amine on the particle surface, or any other suitable functional groups that can link the receptors to the nanoparticles. The receptor molecules will react with the chemical functional group to form a covalent chemical bonding.

Analytes can be any chemical species, biomolecules and biotargets. Chemical species are any natural and synthetic chemical substances (neutral or charged, with or without a confirmed molecular structure), ions such as mercury (II), lead (II), polymers, materials, drugs and pharmaceuticals, drug candidates, or any other chemical substances. Biomolecules are generally biochemical substances, such as proteins, enzymes, antibodies, antigens, haptens, drugs, drug intermediates or fragments, hormones, polysaccharides, metabolites, nucleic acids. Biotargets are biological species or living systems, such as bacteria, virus or related components. The sample that is to be assayed using the invention described can be biological or non-biological based. The biological sample can be, but is not limited to, human and other animal blood, plasma, serum, urine, saliva, sputum, or other bodily fluids; cell supernatants, cell media, or cell lysate; tissue extracts. The non-biological samples can be, but are not limited to, water from different resources, liquid extracts from different materials and objects, etc. The sample solution may or may not need to be pre-processed chemically or physically before conducting the assay. The processing is to eliminate large particles or other factors that may interfere significantly with the assay results. Examples of physical processing include filtration, centrifuge, ultrasonication, precipitation, heating or cooling etc. Examples of chemical processing include adding a chemical or chemicals such as sample diluents, surfactants, oxidation or reduction reagents, disinfectants, cell lysing reagents, denaturing and de-hybridization agents to pre-treat the samples. The amount of the sample used for the assay can vary from nanoliters to microliters. A portion of the sample solution may be divided into multiple smaller portions of samples using a liquid handling system or micro or nanofluidic device for multiple analysis.

DLS is a technique used widely for particle size and size distribution studies (Berne, B. J.; Pecora, R. *Dynamic light scattering: with applications to chemistry, biology, and physics;* 1976, by Wiley: New York). The principal of DLS has been established more than three decades ago and a wide range of DLS instruments and systems are commercially available. This technique is based on the Brownian motion of spherical particles which causes a Doppler shift of incident laser light. The diffusion coefficient of particles are measured and the size of the particles is calculated according to the Stokes-Einstein relation. Although studies have been reported on bioconjugation of metal (e.g. gold) nanoparticles and biomolecular interaction-directed nanoparticle aggregation, prior to the present invention, DLS has not been disclosed in conjunction with metal (e.g. gold) nanoparticle probes for homogeneous and quantitative assays. Applied to the embodiments of the present invention, DLS can detect particle size change, or size distribution change caused by the formation of nanoparticle dimers, trimers, oligomers, and aggregates. This capability makes DLS a suitable analytical tool for a quantitative assay according to embodiments of the invention.

Metal nanoparticles used in the invention can be monodispersed or polydispersed in terms of size. "Poly-dispersed" means the nanoparticle solution contains nanoparticle with different size ranges, while "monodispersed" means all nanoparticles have the same or similar sizes. The metal nanoparticles used in the invention generally have an average size in diameter in the range of 1-1000 nm. The nanoparticles generally have a layer of molecules, ions, or polymers attached covalently or non-covalently on the particle surface to prevent nanoparticle from destabilization. These molecules, ions and polymer may or may not have thiol groups or amine groups in them. Thiol and amine groups have high affinity towards gold nanoparticles. Other molecules with high affinity for gold and silver nanoparticles may be used. Citrate is a common ligand used to protect and stabilize gold and silver nanoparticles. The citrate molecules bind with gold and silver nanoparticles through electrostatic interactions. The preparation of gold nanoparticles or colloids stabilized by citrate molecules was established more than 5 decades ago and has been used since then (Turkevitch, J.; Stevenson, P. C.; Hiller, J. *Discuss. Faraday Soc.* 1951, 11, 55; and Frenz, G. *Nature Phys. Sci.* 1973, 241, 20.) Polymers or smaller oligomers such as oligo(ethylene oxide) (OEG) or poly(ethylene oxide) (PEG) with one or multiple thiol groups on the polymers are also used to modify gold and silver nanoparticle surface. OEG or PEG-protected gold nanoparticles are much more stable than citrate-stabilized nanoparticles in high salt content solutions such as human blood and other biological fluids. The typical salt concentration of these biological fluids is about 100-200 mM.

A new metal particle is also described herein. This metal particle has a layer of poly(acrylic acid) (PAA) attached to the particle surface. The PAA are attached to nanoparticles through non-covalent interactions such as electrostatic, van der Waals interactions and hydrogen bonding. Similar to OEG and PEG-protected nanoparticles, PAA-protected nanoparticles are also much more stable in high salt content solutions.

New methods are also described regarding how to extract an analyte (e.g. antigen) concentration from DLS analysis. The method described obtaining quantitative data from DLS measurements.

The present invention is not limited to the disclosure above or examples provided below. The invention can be used for other applications, for example, embodiments of the invention can generally be used for the detection of any chemical, biological molecule or substance that can cause nanoparticle aggregation or deaggregation after metal (e.g. gold) nanoparticles are modified with appropriate receptors towards these species. As noted above, other than gold nanoparticles, embodiments of the invention may also use silver nanoparticles or other types of nanoparticles that provide large scattering cross section and are detectable at very low concentration using DLS technique. Moreover, the invention is not limited to the detection of chemicals and biological molecules in biological samples. It may also be used for detection of chemical substances in non-biological samples.

EXAMPLES

The Examples provided below are all non-limiting examples. Specific materials disclosed are only exemplary materials. For example, the metal nanoparticles are not restricted to gold nanoparticles (GNP), the analyte are not limited to biomolecules.

Example 1

A One-step homogeneous immunoassay for cancer biomarker protein detection

Millions of people around the world face the risk of cancer, which have been one of the leading causes of mortality. An early detection of cancer can significantly improve the treatment and survival rate of cancer patients. As tumor develops, the cells, tissues and organs can release, increase or decrease the release of certain chemicals in the circulating blood system. These specific chemicals are called biomarkers. Biomarkers detection and monitoring has tremendous significance for cancer diagnosis and treatment.

An ideal immunoassay technique for biomarker detection is expected to meet the following 4-S criteria: simple, highly sensitive, highly specific, and requires small volume of samples. Despite the existence of numerous assay and sensor technologies, an ideal bioanalytical tool that meets all these criteria has yet to be developed. Most bioassay techniques or biosensors either lack the high sensitivity, involve large volume of samples, and/or complicated assay procedures/data analysis that can only be done by trained professionals. A typical heterogeneous sandwich-type immunoassay such as ELISA, chemiluminescence immunoassay, involves the antibody immobilization, multiple steps of incubation and washing cycles, followed by signal amplification and reading. From the initial antibody immobilization to the final reading of the assay results, the entire immunoassay can usually take hours to days to complete. A traditional immunoassay is rather time-consuming and labor-intensive. Although in medical testing labs, these assays are all done by fully automated instruments, such instruments are bulky, expensive to manufacture and to maintain due to complicated assay procedures. Such systems are not suitable for point-of-care purposes and for individual research labs. Also, a typical plate immunoassay requires relatively large volume of samples (50 to 100s μL), therefore, is not suitable for a single drop of blood analysis. Protein microarrays have been developed to minimize the amount of samples needed for the assay, with another distinctive advantage of multiplexing capability. However, protein microarrays involve the use of sophisticated software for data analysis, and the cost for assay development and validation is prohibitively too high for routine purpose and for most research labs to adopt for biomarker research.

As illustrated in FIG. 1, embodiment A, gold nanoparticles (GNP) in the size range of about 1-1000 nm with a large light scattering cross section, are used as an optical probe to couple with an antibody pair (capture and detector antibody, cAb and dAb) for a specific cancer biomarker. These two nanoparticle probes (GNP-cAb and GNP-dAb) are then mixed with a sample solution, which may or may not need to be pre-filtered or chemically treated to remove large particles. In the presence of antigen, the antigen-antibody binding will lead to nanoparticle aggregation. The formation of nanoparticle aggregates versus individual nanoparticle probes can be quantified by DLS, and this quantitative information can be correlated to the antigen concentration. Alternatively, if the distribution peaks of individual particles and particle aggregates are not separated, then the average particle size (for example, it can be expressed as hydrodynamic diameter) increase due to aggregate formation will be used to correlate with the antigen concentration.

Gold nanoparticles, including spherical particles, nanorods and nanoshells with a size ranging from 10s to 100s nanometers, are known to have a large light absorption and scattering cross section in the surface plasmon resonance (SPR) wavelength region. In normalized terms, the scattering cross section of a 30 nm gold particle at its SPR region is about 250 times larger than a 30 nm polystyrene particle. As compared to fluorophores, the scattering light intensity from a 60 nm gold nanoparticle is four to five orders of magnitude higher than a strongly fluorescent fluorescein molecule (Yguerabide, J.; Yguerabide, E. E. *Anal. Biochem.* 1998, 262, 137.).

Dynamic light scattering (DLS), also known as photon correlation spectroscopy or quasi elastic light scattering, is a technique used widely for particle size and size distribution analysis. This technique is based on the Brownian motion of spherical particles which causes a Doppler shift of incident laser light. The diffusion coefficients of particles are measured and the size of the particles is calculated according to the Stokes-Einstein relation. Although a very limited number of studies have been reported more than three decades ago to use DLS for quantitative and homogeneous immunoassay, in these previous works, polymer latex particles were used as light scattering enhancer to conjugate with antibody as the optical probe (Cohen, R. J.; Benedek, G. B. Immunochemistry 1975, 12, 963-966. Von Schulthess, G. K.; Cohen, R. J.; Benedek, G. B. Immunochemistry 1976, 13, 963-966). Compared to gold nanoparticles at similar sizes, the scattering of polymer latex particles is much weaker. This low scattering intensity is not sufficient to suppress the scattering signal from other particles in the sample solution, making this light scattering immunoassay technique unsuitable or significantly limited for detection of low abundance protein analyte. By using gold nanoparticles as the probe, the scattered light intensity from gold nanoparticle probes is sufficiently strong enough to suppress the background light scattering arising from the sample solution, therefore, providing much enhanced sensitivity to the immunoassay.

Figure 4:
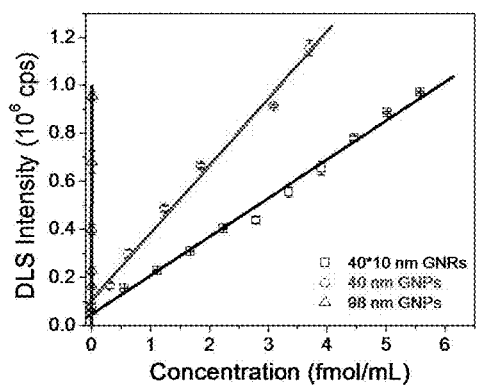
FIG. 4 is the average scattered light intensity of a gold nanorod (GNR, dimension of 10 by 40 nm), 40 nm (GNP40), and 98 nm (GNP98) spherical gold nanoparticles measured at different concentrations by DLS.

The inventors first developed a homogeneous one-step immunoassay for prostate cancer biomarker detection using the embodiment A as illustrated in FIG. 1 (Huo, Q. et al. J. Am. Chem. Soc. 2008, 130, 2780-2782). In this work, a spherical gold nanoparticle with a diameter of 40 nm and a gold nanorod with a dimension of 10 by 40 nm were used to prepare the matched antibody conjugate probes. In a feasibility study, the inventors analyzed the detection limit of gold nanoparticles and nanorods using DLS. FIG. 4 shows the average scattered light intensity of a gold nanorod (GNR, dimension of 10 by 40 nm), 37 nm (GNP37), and 98 nm (GNP98) spherical gold nanoparticles measured at different concentrations by DLS. From this data, the detection limit of three gold nanoparticle materials: GNR, GNP37, and GNP98, was determined to be 0.4 pM, 0.02 pM and 0.7 fM, respectively. This high sensitivity makes gold nanoparticles as very attractive light scattering probes for immunoassays according to embodiments of the invention.

Based on the principal as outlined in FIG. 1, the inventors developed an immunoassay using the invention to detect free prostate specific antigen (free PSA), a biomarker protein associated with prostate cancer. Prostate specific antigen (PSA) is an FDA-approved biomarker for prostate cancer diagnosis. The total PSA concentration of a healthy male is in the range of a few ng/mL and the free PSA (f-PSA) concentration is typically less than 1 ng/mL, in the range of 10-25% of the total PSA. Free PSA is the unbound form of prostate specific antigen. Studies have shown that the percentage of f-PSA in total PSA is lower in patients with prostate cancer than those with benign prostate hyperplasia. The free PSA level is now being introduced and studied as an additional biomarker for prostate cancer screening and diagnosis.

Figure 5:
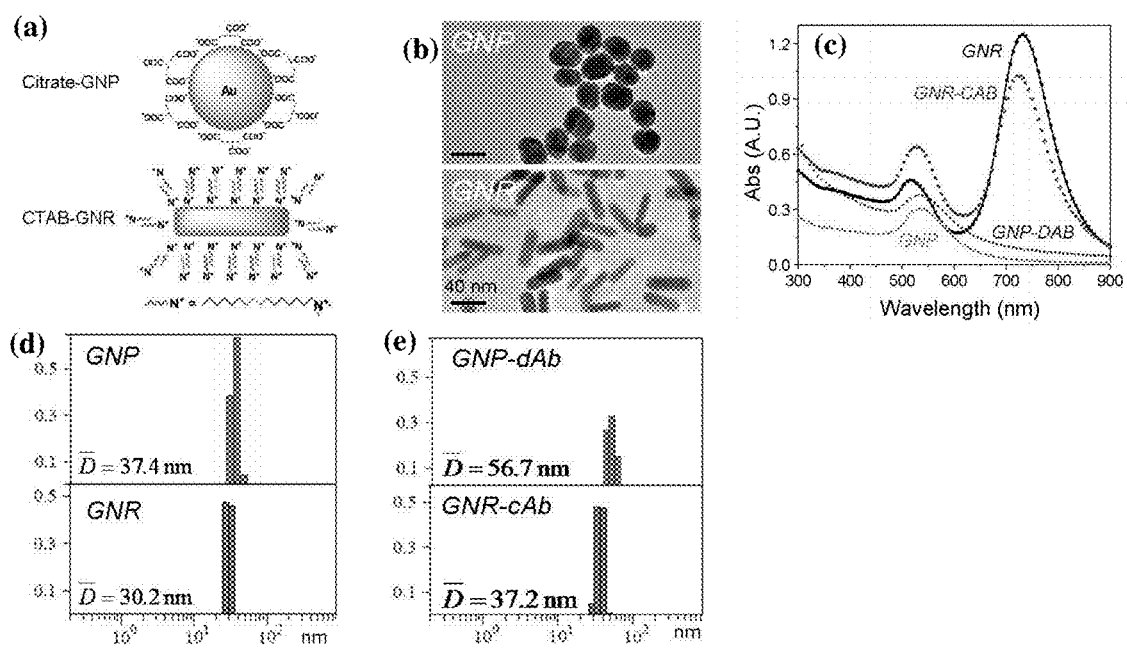
FIG. 5 shows: (a) The chemical structures and (b) TEM images of GNP and GNR particles. (c) The UV-Vis absorption spectra of GNP, GNR probes and their conjugates with an antibody pair: GNP-dAb and GNR-cAb. The two antibodies are anti-free PSA antibodies. (d) The size distribution measured from DLS of unconjugated GNP, GNR, and (e) their conjugates with antibody pairs.

In this study, the inventors prepared two types of gold nanoparticles: one is a citrate-stabilized spherical gold nanoparticle (Ct-GNP, diameter 37 nm), and another one is a cetyltrimethyl ammonium bromide (CTAB)-protected gold nanorod (CTAB-GNR, 10 by 40 nm) (FIG. 5a). The two antibodies were conjugated to the two nanoparticles by non-covalent adsorption. This process is known and familiar to those who are skilled in this field. A TEM image and UV-Vis absorption spectra of GNP and GNR are shown in FIGS. 5b and c. The particle size and size distribution was analyzed by DLS (FIG. 5d). The successful conjugation of nanoparticles with detector antibody and nanorods with capture antibody was first confirmed by UV-Vis spectral analysis and DLS measurement (FIGS. 5c and e). Compared to the original GNPs and GNRs, the SPR absorption band of the nanoparticles were shifted slightly due to the surface chemistry change of the conjugated particles. The size of the conjugated nanoparticles also increased from 37 to 57 nm and 30 to 37 nm, respectively, for the GNPs and GNRs. These data suggest that the two antibody were successfully conjugated to GNP and GNRs respectively. It is estimated that the number of antibody attached to the nanoparticle surface is between 10-100 per particle. Larger particle size will lead to attachment of more antibodies to the particle surface.

The homogenous immunoassay of f-PSA was then conducted in solution using the conjugated nanoparticles and nanorods. The two nanoprobes were mixed in 1:2.5 (GNP-dAb:GNR-cAb) ratio and then added to the standard f-PSA solutions with different concentrations. The GNR probe was added in excess and used as an internal reference. The assay solution was incubated at room temperature for 30 min before DLS analysis. DLS analysis was conducted on a Cool Batch40 system from Precision Detector, Inc.

Figure 6:
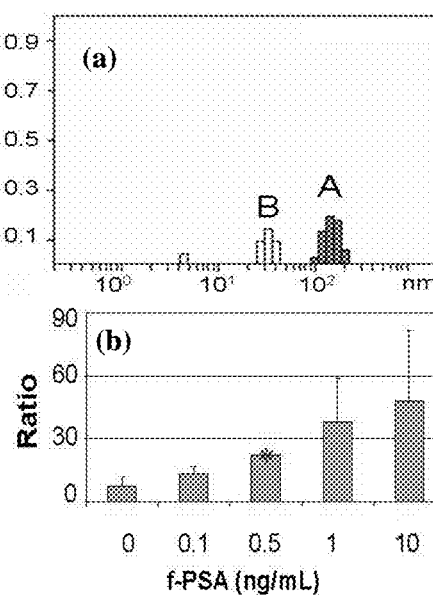
FIG. 6 shows DLS data in particle size distribution of an assay solution with 1.0 ng/mL of f-PSA in sample solution (a). The assay results of f-PSA standard solutions (b) obtained from DLS analysis. The assay results are expressed as the numerical ratio of area A versus area B as shown in (a).

FIG. 6a is a typical size distribution of mixed nanoprobe solution in the presence of 1 ng/mL of f-PSA. For the pure nanoparticle and nanorod conjugates, only one size distribution of particles was observed from the distribution, as seen from FIG. 5e. With f-PSA added to the nanoprobe solution, DLS measurement detected two groups of particle sizes (FIG. 6a, peak area A and B), one is centered at below 60 nm representing individual nanoparticles and nanorods (area B), and one above 100 nm corresponding to nanoparticle-nanorod oligomers (area A). The relative ratio (here we used the scattered light intensity ratio) of nanoparticle oligomers in the size range of 60-500 nm (area A) versus individual nanoparticles in the size range of 20-60 nm range (area B) can be numerically calculated from the size distribution curve. FIG. 6b is the plot of this numerical ratio versus f-PSA concentration. With increased concentration of f-PSA, the relative percentage of nanoparticle oligomers increased while the percentage of individual nanoprobes decreased. Using the same nanoprobes in buffer solution, we conducted the analysis of an unknown sample solution (f-PSA concentration at 0.5 ng/mL). The determined concentration corresponds very well to the true concentration of the sample (FIG. 6b, data indicated with a red asterisk).

The immunoassay demonstrated by the inventors offers several incomparable advantages over traditional immunoassay and other state-of-the-art bioanalytical techniques: (1) an extremely simple assay process; (2) requires minute amount of samples (0.1 to several μL) for the assay, which means we can detect multiple biomarkers from a single drop of blood sample taken from a finger tip; (3) high sensitivity (fM to aM in concentration, or fg in absolute mass) without any amplification steps; (4) low cost with high throughput analysis capability; (5) extremely fast analysis time (a complete assay can be done in less than 5 minutes).

Example 2

Improved homogeneous immunoassay using new robust gold nanoparticle probes

Figure 7:
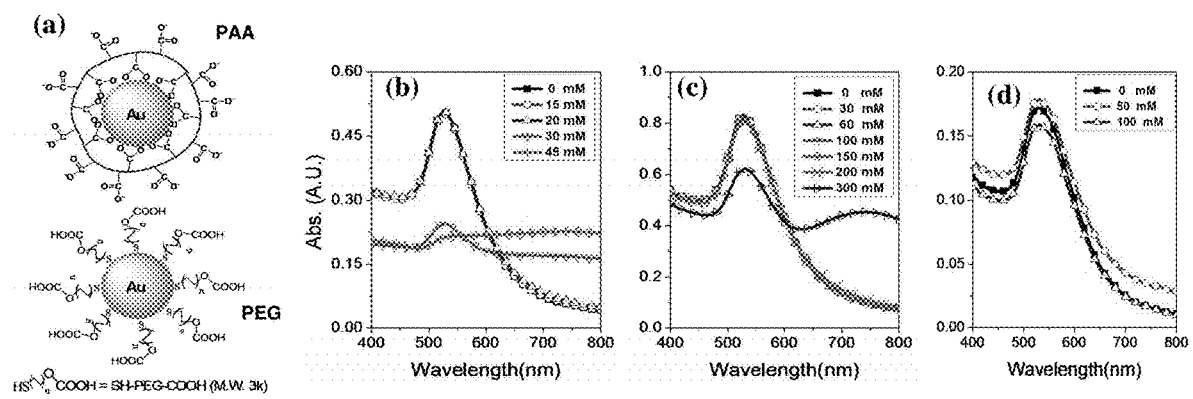
FIG. 7 shows: (a) The chemical structures of PAA-GNP (top) and PEG-GNP (bottom). The UV-Vis absorption spectra of citrate-GNP (b), PAA-GNP (c) and PEG-GNP (d) at PBS buffer solutions (pH 7.4) with different concentrations of NaCl (legends are NaCl concentrations)

Development of robust gold nanoparticle probes: Two new nanoparticle probes with improved stability in high ionic strength buffer solutions than citrate-stabilized gold nanoparticles were developed. One is a spherical gold nanoparticle stabilized by poly(acrylic acid) (PAA) and another one is a thiolated poly(ethylene glycol) ligand (PEG)-stabilized gold nanoparticle (FIG. 7a). Both nanoparticles were obtained from the surface modification of citrate-stabilized gold nanoparticles. The PEG-protected GNPs were synthesized according to the following procedure: Citrate-protected GNPs with an average core diameter of 30-35 nm were first synthesized according to a reported method (Turkevitch, J.; Stevenson, P. C.; Hiller, J. *Discuss. Faraday Soc.* 1951, 11, 55; and Frenz, G. *Nature Phys. Sci.* 1973, 241, 20.). Then 1 mL aqueous solution of a thiolated and bifunctional PEG ligand as shown in FIG. 7, HS-PEG-000H (MW of PEG: 3000, from Rapp Polymers) ($2\times10^{-4}$ M) was added drop wise into 10 mL of citrate-protected GNPs solution. The mixture was allowed to shake at room temperature overnight. The HS-PEG-COOH ligand functionalized GNPs were purified by centrifuge and washed with deionized water three times. The PEG-GNPs were suspended in pure de-ionized water for further use.

The PAA-protected GNPs were synthesized according to the following procedure: 1.5 mL of sodium citrate solution (38.8 mM) was added quickly into a boiling aqueous solution of $HAuCl_4$ (0.35 mM, 100 mL) under vigorous stirring. After boiling for 15 min, 2 mL of PAA aqueous solution (27 mg/mL, pH: ~3) was added drop wise to the above solution. The mixture was allowed to continue boiling for 4 hours. After the solution was cooled to room temperature, the nanoparticle product was concentrated by centrifuge, washed thoroughly with deionized water twice, followed by washing with a diluted NaOH solution (pH: 10) twice. The PAA-modified GNPs were then redispersed in deionized (DI) water for further use A stability comparison study was undertaken on citrate-stabilized, PAA and PEG-stabilized gold nanoparticles in buffer solutions with different salt concentrations using UV-Vis absorption spectroscopy (FIGS. 7b, c and d, respectively). When gold nanoparticles start to aggregate, the surface plasmon resonance band will shift and become broadened. According to UV-Vis spectra as shown in FIG. 7, PAA-stabilized GNPs remain stable in a PBS buffer solution with a NaCl concentration up to 150 mM for 24 hours without significant aggregation, while citrate-stabilized gold nanoparticles aggregate severely at a salt concentration of 30 mM. The PEG-protected GNPs can exist in a buffer solution with a NaCl concentration of 100 mM without significant aggregation. The significantly increased stability of PAA and PEG-protected gold nanoparticles was further confirmed by size analysis using DLS (data not shown here). The physiological salt concentration of human blood is in the range of 100-150 mM. Both PAA and PEG-protected gold nanoparticles synthesized in our study can be suitable as a nanoprobe for future assay of biological samples.

Figure 8:
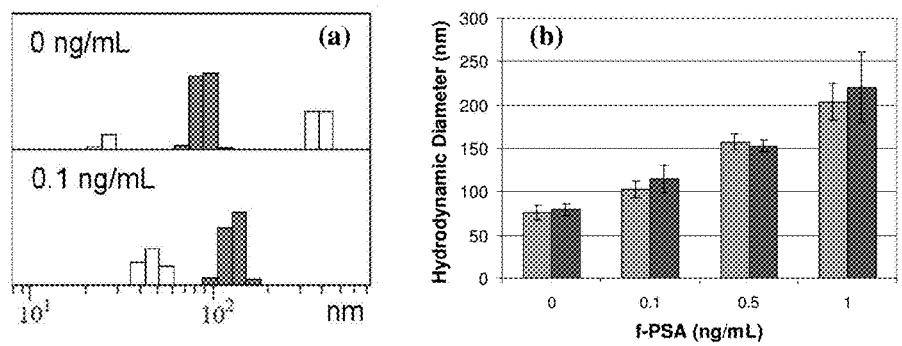
FIG. 8. shows: (a) DLS data (particle size distribution) of the assay solution with 0 and 0.1 ng/mL f-PSA in solution. (b) The plots of hydrodynamic diameters of nanoparticles versus f-PSA concentration. Two sets of assays were conducted. The assay showed both good intra-assay and inter-assay reproducibility. Results were obtained from the Cool Batch40 DLS system from Precision Detectors, Inc.

Both PAA and PEG-protected GNPs were used to conjugate with anti-f-PSA antibody pairs and an immunoassay of f-PSA conducted. Very similar immunoassay results were obtained from both nanoparticle conjugates, but only data from PEG-GNPs are presented here as an illustration. The conjugation of antibody pairs for PAA-GNPs was done through a simple non-covalent adsorption, similar to conjugating antibody to citrate-protected GNPs. The conjugation of antibody pairs to PEG-GNPs was done by covalent chemistry through amide bond linkage. After conjugation, the average diameter of the nanoparticles increased in average by 10-15 nm, corresponding to the expected size increase from PEG-GNPs or PAA-GNPs covered with a layer of antibody. Immunoassay of f-PSA in standard solution was then conducted using these nanoparticle probes. For this assay, PEG-GNPs conjugated with capture and detector anti-f-PSA antibody were mixed in equal amount and the average nanoparticle size increase caused by nanoparticle aggregation was monitored and analyzed by DLS. FIG. 8a is the size distribution of nanoparticles in the assay solution with 0 ng/mL and 0.1 ng/mL f-PSA present, and FIG. 8b pertain to the assay results from two different experiments. From FIG. 8a, one can see that when analyte f-PSA is present, the average particle size of the assay solution is increased compare to assay solution that has no analyte f-PSA in the sample solution (compare the two dark grey-colored distribution peaks, the white-colored particle distribution peaks are from impurities). The average particle size (here expressed as the hydrodynamic diameter) increases proportionally with increased analyte concentration, as seen from FIG. 8b. The assay of each sample solution was conducted in duplicates. The standard deviation of each concentration tested is very small, indicating excellent intra-assay reproducibility, while the inter-assay reproducibility is also very good.

The following seven biomarkers are currently being tested as target analyte for the immunoassay development: free-PSA, total PSA, CA 125, CA 15.3, CA 19-9, Her-2/neu and CEA. These biomarkers are associated with one or more of the following cancers: prostate, breast, ovarian, pancreatic, liver, lung and colorectal cancer. Other than CEA, all other biomarkers are FDA-approved serum biomarkers. The method described herein can be essentially applied to any biomarker. Thus, the bioassay technique described herein is not limited to these particular cancer biomarkers. It may also be extended to the analysis of other proteins, antibodies, antigens, DNAs, RNAs, as well as other biological targets.

Example 3

Figure 9:
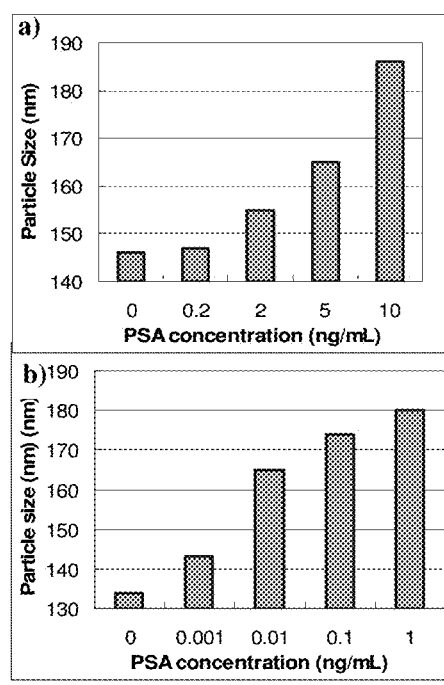
FIG. 9 shows assay results for total PSA in standard solutions using 100 nm GNP antibody conjugate probes. The 100 nm GNP probes were prepared by non-covalently adsorbing a matched monoclonal anti-total PSA antibody pairs to two batches of gold nanoparticles. The assay results were expressed as average particle size diameter of the assay solution. The assays were done in two different concentration ranges: (a) 0.2-10 ng/mL and (b) 0.001 to 1 ng/mL.

Development of a One-step homogeneous immunoassay with improved sensitivity and dynamic range: As shown in FIG. 4, the light scattering intensity from a 100 nm GNP is substantially higher than a 40 nm GNP. Most recently, using GNPs with an average core diameter of 100 nm, we prepared a set of nanoparticle probes for total prostate specific antigen (PSA) detection. The average particle size (or so-called hydrodynamic diameter of the particles) of the assay solution was recorded to determine the analyte concentration. The two matched antibody for total PSA were conjugated to citrate-protected 100 nm GNPs to form two nanoparticle probes. Using this set of new probes, we were able to detect total PSA at a concentration as low as 1 pg/mL and extend the dynamic range of the assay to two concentration ranges: 0.1-10 and 0.001-1 ng/mL (FIGS. 9a and b, the two dynamic ranges were obtained by adjusting different amount of samples added to the nanoprobe solution: (a) 2 µL sample was added to 40 µL of probe solution; (b) 20 µL of sample was mixed with 20 µL of probe solution). While the high concentration range may be used for routine screening purpose, the low concentration range may be used for monitoring cancer recurrence after prostatectomy.

Figure 10:
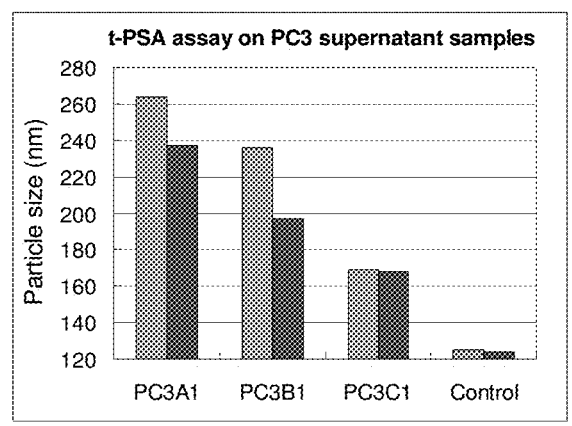
FIG. 10 shows assay results in duplicate for total PSA secreted by PC3 cells in the supernatants using 100 nm GNP antibody conjugate probes. The results were expressed in average particle size. The 100 nm GNP probes were prepared by non-covalently adsorbing a matched monoclonal anti-total PSA antibody pairs to two batches of gold nanoparticles. The cell supernatants were collected after 24 hours of growth. Samples PC3A1, PC3B1, and PC3C1 had approximately 1 million, 500K and 250K cells in the culture dish. To conduct the assay, 2 μL of cell supernatant was added to 40 µL of mixed nanoprobe solution. After incubating the solution at room temperature for 5-10 min, results were read by DLS.

Additionally, we used this assay to detect PSA secreted from prostate cancer cells, PC3, in cell supernatants collected after 24 hours of growth. The results are shown in FIG. 10. Samples PC3A1, PC3B1, and PC3C1 had approximately 1 million, 500K and 250K cells in the culture dish. To conduct the assay, we simply added 2 µL of cell supernatant to 40 µL of mixed nanoprobe solution. After incubating the solution at room temperature for 5-10 min, results were read by DLS in less than 1 min. Comparing PC3A1, PC3B1, and PC3C1, the difference in PSA level can be clearly seen (FIG. 10). The reproducibility of the assay is very good (data shown in FIG. 10 are duplicates), and assays conducted using different batches of nanoprobes are also very reproducible. We used a commercial available total PSA ELISA kit (Anogen) to test these three cell supernatant samples. The kit was not able to detect PSA at all from all three samples (the validity of the assay kit was confirmed by assay of standard PSA solution included in the kit as well as a number of human serum samples). These results clearly demonstrated the unmatched superiority of the new assay described in this invention compared to commercial immunoassay products.

Figure 11:
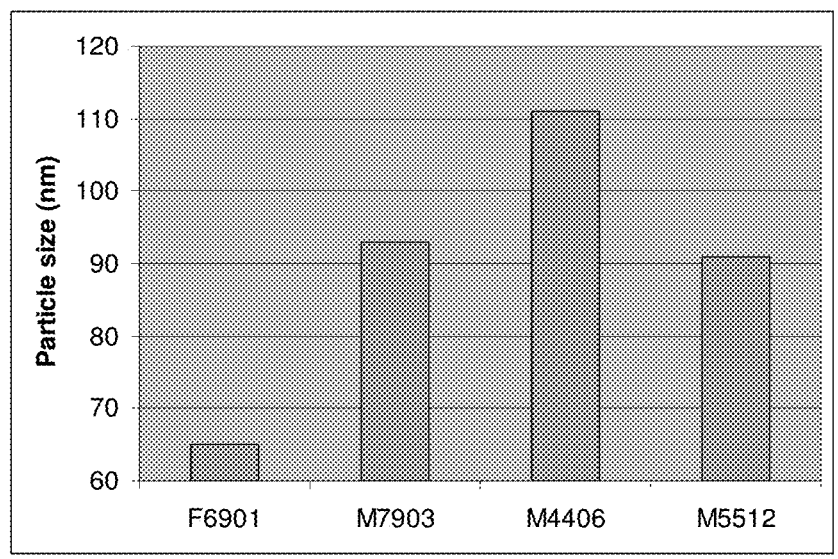
FIG. 11 is the assay results of four human serum samples using the same probes as described in FIG. 7 and FIG. 8.

Using the 100 nm GNP probes, the inventors also analyzed the relative level of total PSA from four different human serum samples: F6901, M7903, M4406, and M5512. The particle size analysis results of the assay solutions are shown in FIG. 11. "F" means the subject is a female and "M" means the subject is male. These human subjects are known as normally healthy and have not been diagnosed with prostate cancer. The first two digits in the sample name is the year when the subject was born. From the particle size analysis results, the order of total PSA level should be: M4406>M7903≅M5512>>F6901. M5512 has a clinically determined total PSA level of 0.6 ng/mL. This order of total PSA level reflects roughly the total PSA level difference between females and males, and males at different ages. Females should not have or have extremely low level of PSA, which PSA level increases on males whose age is over 60-65. Although the absolute value of total PSA level has yet to be determined through the establishment of an accurate calibration curve, so far these results indicate that the immunoassay as described in this invention can be used for analyte detection from human blood and serum samples.

Example 4

Figure 12:
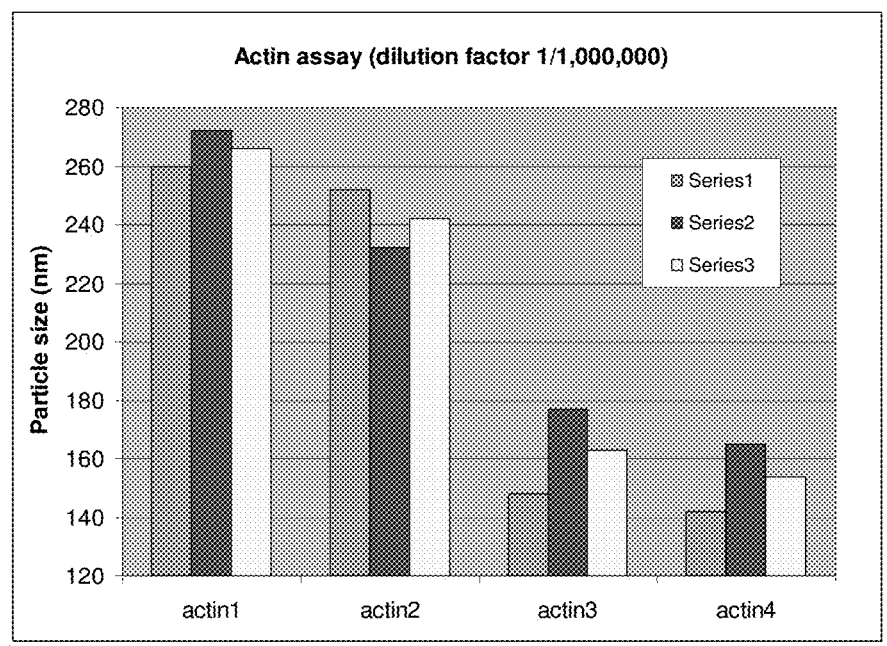
FIG. 12 is the assay results of four sample solutions that contain actin at a concentration of 34.5, 17.3, 8.6, and 4.3 ng/mL of actin, respectively. The actin solutions were cell lysates. The two probes were prepared by conjugating a matched monoclonal anti-actin antibody to two batches of 100 nm GNPs. The first two columns (blue and dark red) are DLS data in average particle size from two different assays and the third column (light yellow) is the average of the two assay results.

Immunoassay for actin using the One-step homogeneous immunoassay as described in this invention: Actin is a major component of both the cytoskeletal and contractile structures in all cell types. It varies in amount, being related to the type of differentiation and to the functional state of cells and tissues. Actin can be found in two different forms, the globular or the fibrillar state. Actin is often used in Western blot as a standard protein solution to monitor the success of the Western blot. By conjugating a matched pair of monoclonal antibody with 100 nm GNPs, the inventors developed two probes for homogeneous assay of actin using dynamic light scattering. FIG. 12 is the assay results of a series of actin solutions. The results correspond well to the results obtained from Western blot. The concentrations of the four samples, actin1 to actin4, are approximately 34.5, 17.3, 8.6, and 4.3 mg/mL respectively, for the Western blot analysis. The detection limit of actin by Western blot is roughly at 2 mg/mL. These four samples were diluted 1 million times to 34.5, 17.3, 8.6, and 4.3 ng/mL respectively, for the homogeneous immunoassay using the invention as described herein. As seen from FIG. 12, the difference between the four actin samples can be clearly seen. The sensitivity of the homogeneous immunoassay disclosed in this invention is about six orders of magnitude higher than the traditional Western blot. The amount of the sample solution used in the present assay (2-5 microliters) is also substantially smaller what needs to be used (100s microliters) for Western blot analysis.

Example 5

A One-step competitive and non-competitive assay for mouse IgG Detection Using a Goat Anti-Mouse IgG Gold Nanoparticle Probe: In this example, the inventors developed two formats of assays for mouse IgG (immunoglobulin G) detection using the embodiments B and C as illustrated in FIG. 1. This study demonstrates the possibility of both competitive and non-competitive assay using the described invention. Goat anti-mouse IgG is a secondary antibody that has specific binding affinity towards mouse IgG, a primary antibody. The secondary antibody may bind to the Fab, Fab' or Fc region of the primary antibody, therefore, mouse IgG is considered to have multiple binding sites for the secondary antibody.

Figure 13:
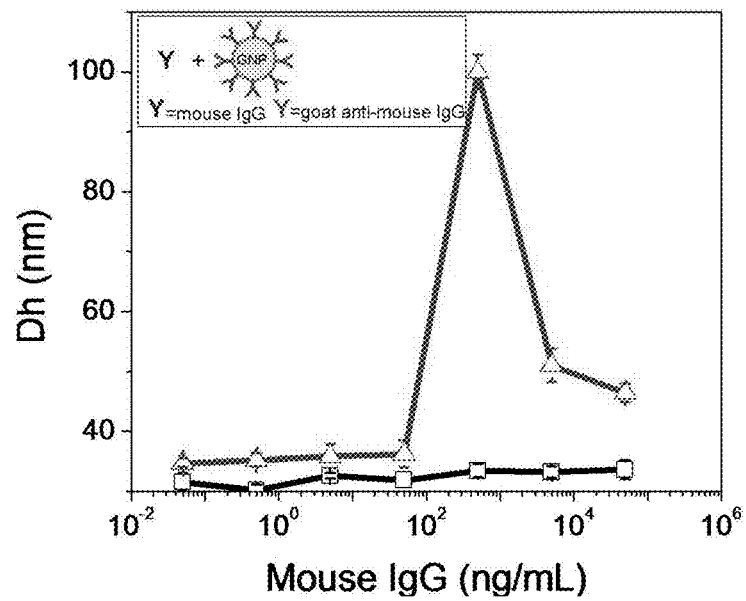
FIG. 13 shows the hydrodynamic diameter (Dh) change of assay solutions of mouse IgG mixed with two different gold nanoparticle probes after incubating at 37° C. for 2 hours. (-□-: a control made of mouse IgG with 0.1 nM BSA conjugated GNPs; -Δ-: mouse IgG mixed with a 0.1 nM goat-anti mouse conjugated GNPs. The assay using BSA conjugated GNP as a control for the study)
Figure 14:
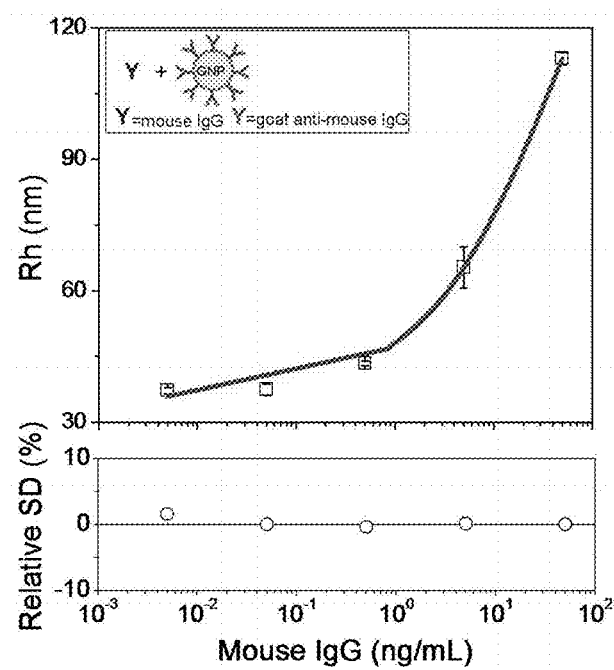
FIG. 14 is the results of a direct assay for mouse IgG detection using 0.01 nM goat anti-mouse IgG conjugated GNPs (GNP-anti-IgG). Measured data was fitted into a logistic model using a four parameter Logistic fitting without weighting. (LLOD=0.0078 ng/mL, 3σ, R=2; y=187.55435+(35.46758−187.55435)/(1+x/46.97037)$^{06302}$, $R^2$=0.9994; error bar: standard deviation.

In a first format of assay that we developed for mouse IgG detection, mouse IgG was directly mixed with goat anti-mouse IgG conjugated GNPs (40 nm, GNP-anti-IgG). The conjugation of goat anti-mouse IgG to GNPs was done by non-covalent adsorption. Due to the multiple binding sites of primary mouse IgG by the secondary antibody, mouse IgG caused nanoparticle aggregation. FIG. 13 is an assay conducted with a probe concentration of 0.1 nM, while FIG. 14 is an assay conducted with a probe concentration at 0.01 nM. In this one-step assay, mouse IgG can be detected at concentrations from 7.8 pg/mL to 50 ng/mL (or approximately 52 fM to 0.33 nM), when the probe concentration was set at 0.01 nM (results from FIG. 14). The detection limit and dynamic range of the assay may be adjusted using different concentration of the nanoparticle probe, as revealed from comparison of FIG. 13 with FIG. 14. This example is an illustration of embodiment B as described in this invention and FIG. 1, using a single type of probe to detect an analyte that has multiple binding sites to the single type of receptor attached to the nanoparticle probe.

Figure 15:
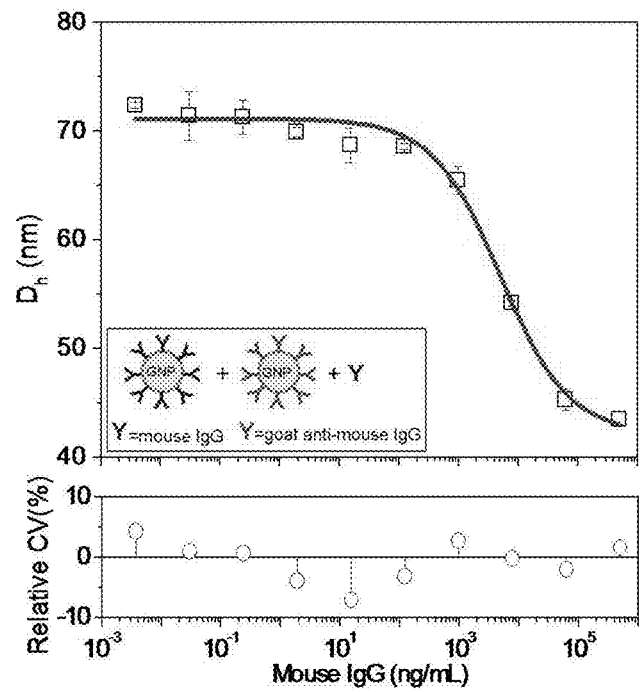
FIG. 15 is the results of a competitive assay for mouse IgG detection using two nanoparticle probes, GNP-IgG and GNP-anti-IgG. Here GNP-anti-IgG serves as the probe, and GNP-IgG serves as an aggregation inducer. Analyte mouse IgG competes with GNP-IgG to bind with GNP-anti-IgG. The concentration of both GNP-anti-IgG and GNP-IgG probes was 0.1 nM. Each assay solution was incubated at room temperature for 4.5 hours. Measured data was fitted into a logistic model using a four parameter Logistic fitting without weighting. (LLOD=283.0036 ng/mL, 3σ, R=2; y=42.21247+(71.12096−42.21247)/(1+x/5023.40461)$^{0.76428}$, $R^2$=0.9895, error bar: standard deviation FIG. 16 is a schematic illustration of a homogeneous detection of DNA using gold nanoparticle probes and dynamic light scattering.

A second format of assay developed in this study is a competitive assay conducted by using both mouse IgG and goat anti-mouse IgG-conjugated GNPs, that is, GNP-IgG and GNP-anti-IgG. The GNP-anti-IgG serves as the probe and GNP-IgG serves as an aggregate inducer to compete with analyte mouse IgG for binding with GNP-anti-IgG. The mouse IgG-conjugated GNP probes were prepared by conjugating biotinylated mouse IgG to a streptavidin-coated GNP. When simply mixing the two GNP probes together in solution in approximately 1:1 mole ratio, the two GNP probes will aggregate together due to specific binding between mouse IgG and goat anti-mouse IgG molecules. The addition of mouse IgG as a target protein in the mixed probe solution caused a reduction of aggregation between two nanoparticle probes. The mouse IgG analyte in solution will bind with the GNP-anti-IgG, therefore, inhibiting the binding of GNP-IgG with GNP-anti-IgG to form aggregates. The reduction of aggregation was then used to correlate with the target protein, mouse IgG, concentration. FIG. 15 shows the assay results expressed as the average particle size of the assay solution in hydrodynamic diameter versus the analyte concentration. An inverse relation is found from the average particle size versus analyte concentration. In this assay, mouse IgG can be detected at a concentration from approximately 100 to 100,000 ng/mL in solution. This competitive assay avoided the problem of "hook effect" as often encountered in non-competitive assays.

Through this study, the inventors demonstrate that gold nanoparticles with their strong light scattering property, can be used as a highly sensitive optical probe to replace traditional polymer latex particles for laser light scattering immunoassay development. The sensitivity and dynamic range of such assays can be adjusted very conveniently to the expected range by selecting appropriate nanoparticle probe concentrations and assay conditions. A single type of probe, or more than one type of probes may be used for the assay. Both competitive and non-competitive assay formats may be considered in the actual assay development for each individual protein analyte.

Example 6

A One-step highly sensitive method for DNA detection using dynamic light scattering. The inventors also demonstrated that this invention can be used for DNA detection and analysis (Huo Q., et al. J. Am. Chem. Soc. 2008, 130, 8138-8139). There is a considerable demand for rapid, low-cost, and sensitive detection of specific DNA sequences for the clinical diagnosis of genetic and pathogenic diseases. Currently fluorescent optical label-based DNA detection methods such as DNA microarray and molecular beacons are dominating the market. However, there are several limitations in these widely adopted methods. One problem is the relatively low signal amplification. Because one DNA probe is labeled with one or a few fluorophores, the fluorescence signal is rather weak when the target DNA concentration is low, leading to relatively poor sensitivity. A second problem is the poor photostability of typical fluorophores. Most organic dyes suffer from serious photobleaching and this often leads to irreproducible results.

To solve some of these problems, several types of nanomaterials such as quantum dots, carbon nanotubes, silicon nanowires, and metallic nanoparticles have been explored as signaling probes for DNA detection. Among them, gold nanoparticles (AuNPs or GNPs) have been used in a variety of forms for detecting DNAs based on their unique size and distance-dependent optical properties. Mirkin and co-workers first developed a colorimetric detection of DNA hybridization in a homogeneous solution based on the formation of oligonucleotide-functionalized AuNPs aggregates in the presence of target DNAs (Elghanian, R.; Storhoff, J. J.; Mucic, R. C.; Letsinger, R. L.; Mirkin, C. A. Science 1997, 277, 1078.) The nanoparticles aggregation can be detected directly by observing the color change of the solution from red to purple, or monitored by UV-Vis absorption spectroscopy. However, the main limitation of this approach is its low sensitivity (10 nM). To increase the sensitivity, DNA bar code amplification and other optical signal amplification techniques such as scanometric method, and surface enhanced Raman spectroscopy (Taton, T. A.; Mirkin, C. A.; Letsinger, R. L. Science 2000, 289, 1757. (b) Cao, Y. W.; Jin, R. C.; Mirkin, C. A. Science 2002, 297, 1536), have been developed to improve the detection limit to femtomolar and attomolar range. However, all these amplification methods involve complicated multiple-step procedures that are not only time consuming, but also often cause problems in reproducibility.

Figure 16:
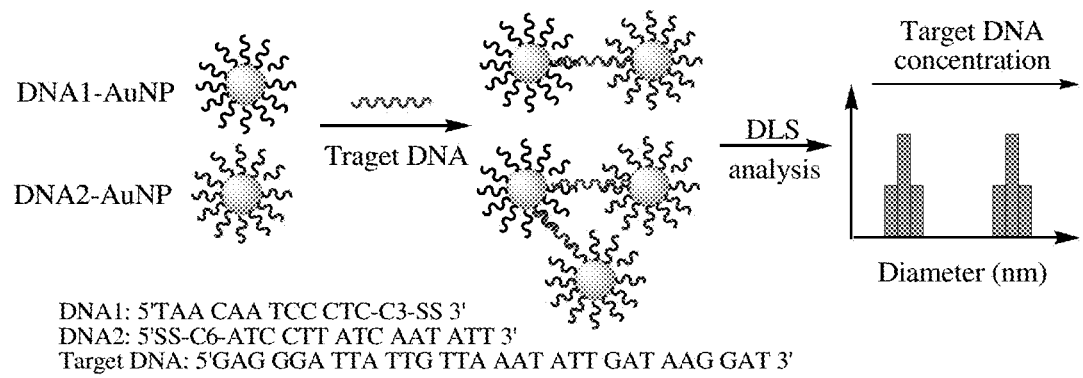

In this work, the inventors applied the invention for DNA detection. As illustrated in FIG. 16, two sets of single stranded DNA probes are functionalized onto citrate-protected gold nanoparticles (DNA1-AuNP and DNA2-AuNP). When the two DNA-functionalized AuNP probes are mixed in a sample solution that contains complementary target DNAs, the hybridization of target DNA with two nanoparticle probes will cause nanoparticles to form dimers, trimers, and larger aggregates. This nanoparticle aggregation will increase the average diameter of the whole nanoparticle population, which can be detected by DLS analysis. The average diameter increase of the nanoparticles can then be correlated quantitatively to the target DNA concentration. A higher target DNA concentration should lead to more extensive nanoparticle aggregation, and larger average nanoparticle size increase as shown in FIG. 16.

Figure 17:
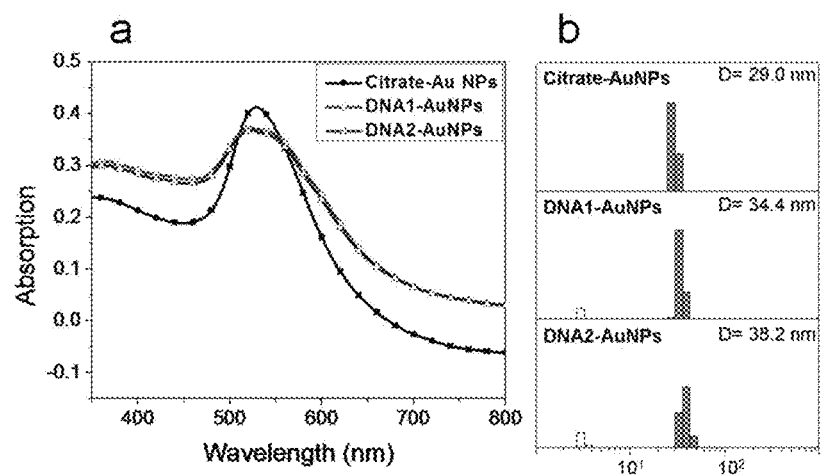
FIG. 17 is the UV-Vis absorption spectra (a) and size distribution (b) of gold nanoparticles (AuNPs) before and after DNA conjugation.

In this work, the inventors synthesized a citrate-stabilized gold nanoparticle with a core diameter of 30 nm according to a reported procedure (Turkevich, J.; Stevenson, P. C.; Hillier, J. Discuss. Faraday Soc. 1951, 11, 55). Two DNA probes as previously used in the work by Mirkin et al., are conjugated to the gold nanoparticles (Jin, R.; Wu, G.; Li, Z.; Mirkin, C. A.; and Schatz, G. C. J. Am. Chem. Soc. 2003, 125, 1643. Stoeva, S. I.; Lee, J. S.; Thaxton, C. S.; and Mirkin, C. A. Angew. Chem. Int. Ed. 2006, 45, 3303). FIG. 17a is the UV-Vis absorption spectra of AuNPs probes before and after conjugating with DNA probes. The AuNP solution was initially pinkish-red with a SPR band at 520 nm. Upon functionalization of single stranded DNA, the SPR band remained at 520 nm, indicating no particle aggregation due to an increased repulsive interaction between nanoparticles after conjugating with single stranded DNAs. DLS measurement was used to monitor the size change of AuNPs before and after conjugating with the two DNA probes. As shown in FIG. 17b, the hydrodynamic diameter of the nanoparticles increased slightly from 29.0 nm to 34.4 nm for DNA1-AuNP and 38.2 nm for DNA2-AuNP, respectively. This hydrodynamic diameter change is caused by the addition of a DNA layer on the nanoparticle surface. The DLS data also revealed a very narrow size distribution of AuNPs before and after DNA modification. Both UV-Vis absorption and DLS measurement indicate that the DNA-AuNP probes remained to be individually dispersed in the solution.

Figure 18:
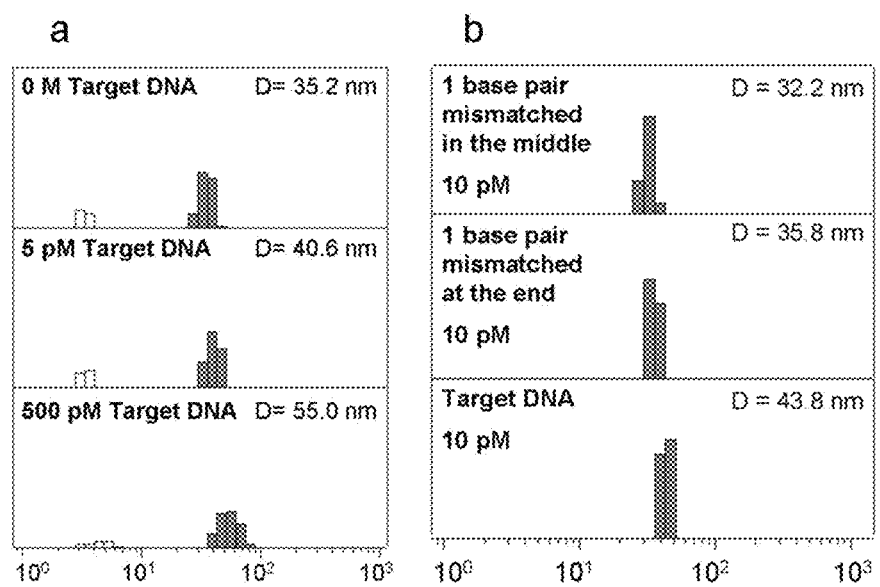
FIG. 18 is the size and size distribution (in diameter, nm) of DNA-AuNP assay solutions in the presence of perfectly matched target DNAs (a), and single base pair-mismatched DNAs at a concentration of 10 pM (b).
Figure 19:
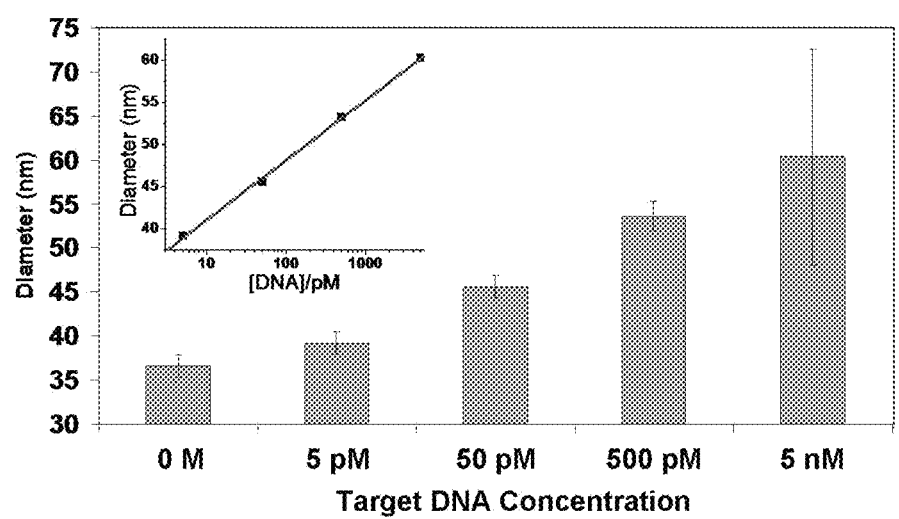
FIG. 19 is the average diameters of the assay solution containing different concentrations of target DNAs as determined from DLS measurements and plotted against the target DNA concentrations.

For target DNA detection, a 1:1 mixture solution of the two DNA-AuNP probes at a concentration of 100 pM was added to a set of target DNA solutions with a concentration ranging from 5 pM to 5 nM. The concentration of DNA-AuNP probes was determined using UV-Vis absorption spectroscopy. The mixed solution was incubated for 5 min at 70° C., and then allowed to cool down to room temperature and set for 2 hours. The solution was then diluted 100 fold for DLS measurement (the DLS sample cell requires a 1-1.5 mL sample solution). As shown in FIG. 18a, the average size of gold nanoparticles in the control sample with 0 M target DNA in solution is around 35.2 nm. In a sample solution containing 5 pM target DNAs, the average nanoparticle size increased to 40.6 nm. The whole nanoparticle population now contains the individually dispersed DNA-AuNP probes, nanoparticle dimers, trimers and oligomers formed due to hybridization between DNA targets and DNA probes. With increased concentration of target DNAs, the average nanoparticle hydrodynamic diameter increased accordingly. FIG. 19 is a plot of the particle size over the target DNA concentration from 5 pM to 5 nM. The detection limit is estimated to be around 1 pM. Without any optimization, this detection limit is already 4 orders of magnitude higher than absorption-based methods as reported previously (Elghanian, R.; Storhoff, J. J.; Mucic, R. C.; Letsinger, R. L.; Mirkin, C. A. *Science* 1997, 277, 1078). The assay exhibits excellent reproducibility, as judged from the small standard deviation of each concentration (three samples were run for each concentration) and a good linearity of the assay (see inset in FIG. 19).

To examine the selectivity of the new assay, the inventors conducted a comparison study on single base pair-mismatched DNAs from perfectly matched DNA targets. Two types of mismatched DNA targets were studied: one with a mismatched pair located at the end and one with a mismatched pair in the middle of the target DNA sequence (mismatched sequences are shown in the Supporting Information of the paper by the inventors, Huo Q., et al. *J. Am. Chem. Soc.* 2008, 130, 8138-8139). Under the exact same assay conditions, DLS analysis revealed a much less degree of nanoparticle aggregation when the target DNA has a single mismatched base pair, judging from the hydrodynamic diameter of the nanoparticles as shown in FIG. 18b. This single base pair mismatch study was conducted at a target DNA concentration of 10 pM. The result demonstrates the capability of our new assay to discriminate single base pair-mismatched DNAs from perfectly matched target DNAs, without using the melting transition of DNA-nanoparticle aggregates as required by a previously reported method (Elghanian, R.; Storhoff, J. J.; Mucic, R. C.; Letsinger, R. L.; Mirkin, C. A. *Science* 1997, 277, 1078).

In conclusion, the inventors demonstrated a one-step homogeneous hybridization assay for DNA detection based on the invention. This assay is extremely easy to conduct, provides much higher sensitivity compared to absorption-based methods, however, without any signal amplification process. Single base pair-mismatched DNAs can be readily discriminated from perfectly complementary DNAs directly from the DLS analysis under ambient conditions.

Example 7

DLS Systems

Figure 2:
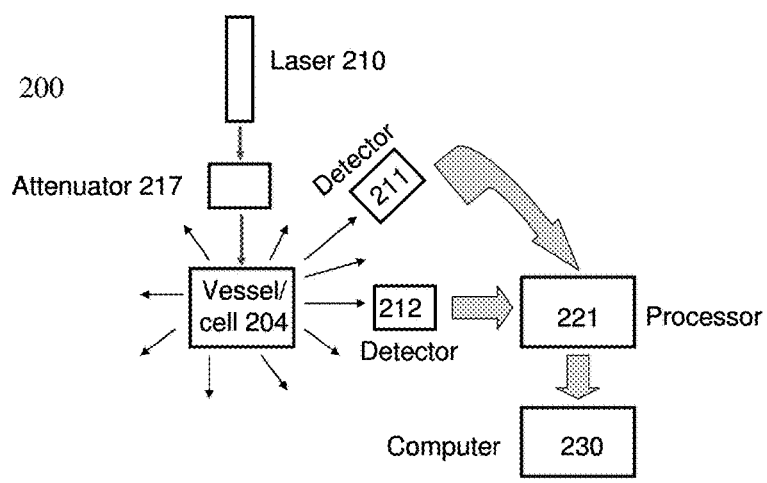
FIG. 2 is a basic design of a DLS system.

FIG. 2 shows a basic DLS system 200 according to the invention for determining the presence of analyte in one sample at a time manually. System 200 comprises a vessel/cell 204 formed from an optically transparent material for holding a sample solution suspected of containing at least one target analyte, and the same or two different nanoprobes conjugated with receptors. The receptors can be the same or different. A light source, such as laser 210 directs light with a suitable wavelength (e.g. ultraviolet, visible, near infrared, or infrared) at the analyte comprising solution which is contained in a vessel/cell 204. An attenuator 217 may or may not be used to adjust the intensity of the incident laser beam from laser 210. At least one detector, such as detectors 211 and 212, is provided for measuring a scattered light signal from the analyte comprising solution. The detector may be placed at different angles in relative to the incident laser beam, from 0 to 180 degree angle, in a more specific embodiment, 0-90 degree. In one embodiment, the analyte detected excludes DNA, or if DNA is the target analyte, the detector relative to the laser must be between 0-90 degrees. At different detector angles, the sensitivity of the assay may vary. A best detector angle should be selected to detect nanoparticle aggregates most sensitively. One example is a forward angle at 13 degree. Other angles may be used as well depending on the type of metal particles used and the assay formats. More than one detector may be used for simultaneous analysis of multiple samples. Outputs from detectors 211 and 212 are shown coupled to a correlator or other type of processor 221 associated with a computer 230 which using correlation software and is operable for determining the particle diffusion coefficients, and/or particle size and/or size distribution from the correlation function. The data collection, processing, analysis and display will be controlled by the computer 230. The computer software will convert the DLS data to analyte concentration information. A linear or non-linear relation exists between the DLS data of the assay solution and the analyte concentration. The absolute analyte concentration may be determined by comparison with a calibration curve obtained using standard analyte solutions with known concentrations. When standard analyte solutions are not available or it is not necessary to obtain the absolute concentration of the analyte, the nanoparticle diffusion coefficients, size and/or size distribution data may be used directly to obtain the relative analyte levels from different samples.

Figure 3A:
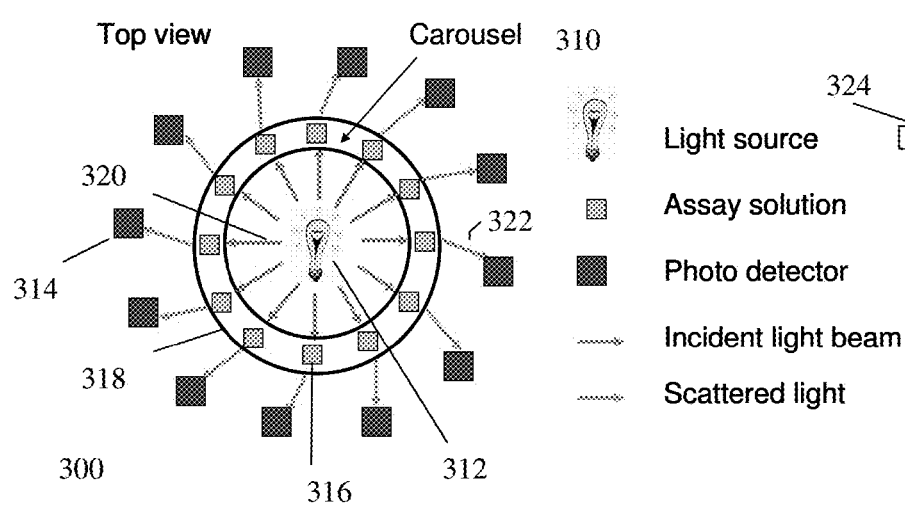
FIG. 3(a), FIG. 3(b) and FIG. 3(c) represent schematic diagrams of DLS system implementing a multiple sample platform for simultaneous DLS measurement of multiple samples using a plurality of detectors (FIG. 3(a), FIG. 3(b)) or continuous DLS measurement of multiple samples using a single detector and a rotatable carousel FIG. 3(c).
Figure 3B:
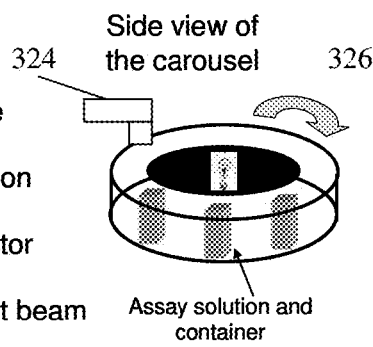
Figure 3C:
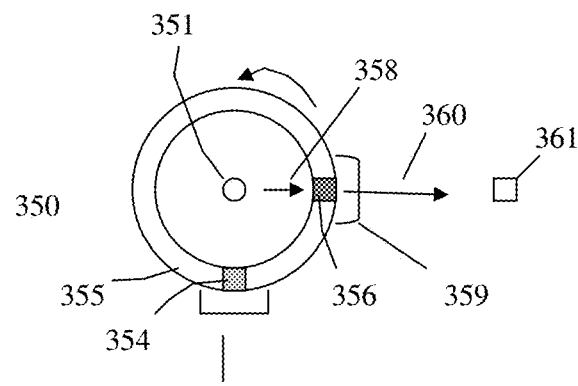

In other more specific embodiments, the invention pertains to DLS systems that are particularly adapted to conduct assay embodiments of multiple samples simultaneously or sequentially through automatic control. An example of such an adapted DLS system with two different setups is illustrated in FIG. 3. The first setup is used to analyze one sample solution at a time (FIG. 3c) and the second setup is used to measure multiple samples (means more than one sample) simultaneously (FIGS. 3a and b). Other than the required components for a basic DLS as shown in FIG. 2, this modified system 300 contains the following additional features/components: (1) a laser beam 312 that can be split into multiple beams (or multiple lasers) as incident light beams 322 for multiple assay solutions 316, to thereby produce a scattered light signal 322; (2) a movable platform 318 such as carousel that can hold one or more than one assay solution containers. FIG. 3 illustrates an example of a carousel 318 that has 12 assay solution containers 316 or cell holders where cells that contain the assay solutions can be loaded to the holder manually or automatically. The carousel 318 may be a stand-alone device. The carousel 318 will be inserted into the DLS main system manually or automatically. The carousel may also rotate in-plane as illustrated in FIG. 3b (326). The system 300 may optionally include a liquid handling system 324 for delivering and/or removing fluid from the cells.

Generally, the DLS is equipped with a single or multiple detectors. The number of detectors may match the number of sample solution containers in the carousel. The number of detectors may be smaller than the number of sample solution containers in the carousel. Each detector will detect the scattered light signal from one sample solution. The data collected from each detector may be processed by the same processor such as correlator sequentially or multiple processors simultaneously to obtain the correlation function of each assay solution. As an example, FIG. 3 illustrates that 12 samples may be analyzed simultaneously using one laser source and 12 detectors. Alternatively, one can turn on only one detector, load one sample to the carousel a time. By rotating the carousel, the user can continuously load a new sample and unload the analyzed sample from the carousel so that multiple samples may be analyzed sequentially. FIG. 3 is only an illustration. Other settings that are based on the sample concept may be adapted as well. For example, the carousel may contain any number of sample solution containers or cell holders other than 12. The carousel may be replaced by a microfluidic device with sample solution containers embedded in the device. The carousel may also be replaced by a device that does not have the circular shape as shown in FIG. 3, but functions the same as a carousel. The different modes as discussed above (fixed carousel versus rotatable carousel using single or multiple detectors simultaneously) may be combined together to speed up the assay and reduce the cost.

Shown in FIG. 3c is an alternative embodiment that provides for a reduction in the amount of DLS detectors needed but also allows the user the ability to manipulate samples in and out of the movable platform expediently. System 350 includes a movable platform 355 that has at least a first container 354 and a second container 356. The movable platform 355 may shift one or the other containers 354, 356 from a load zone 357 to a detection zone 359. The light source 351 sends an incidental light beam 358 at the container in the detection zone 359 to thereby produce a scattered light signal 360. The detector 361 detects the scattered light signal for further processing by a computer.

For both DLS systems, a computer software will be used to control the liquid mixing, sample loading and unloading, and the DLS measurement; to process the scattering light intensity data into correlation function; to process the correlation function data into particle diffusion coefficient, particle size and/or size distribution information; and to process such information into analyte concentration (including relative or absolute concentration) with and without the use of a calibration curve. Calibration curve is established by assaying a series of standard sample solution with known concentration of analyte. Typically, comparison of DLS data obtained from an unknown sample solution with the calibration curve will reveal the analyte concentration in the unknown sample.

As will be appreciated by one of skill in the art, embodiments of the present invention may be embodied as a device or system comprising a processing module, and/or computer program product comprising at least one program code module. Accordingly, the present invention may take the form of an entirely hardware embodiment or an embodiment combining software and hardware aspects. Furthermore, the present invention may include a computer program product on a computer-usable storage medium having computer-usable program code means embodied in the medium. Any suitable computer readable medium may be utilized including hard disks, CD-ROMs, DVDs, optical storage devices, or magnetic storage devices.

The term "processing module" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory device. The memory device may be a single memory device or a plurality of memory devices. Such a memory device may be a read-only memory, random access memory, volatile memory, non-volatile memory, static memory, dynamic memory, flash memory, and/or any device that stores digital information. A computer, as used herein, is a device that comprises at least one processing module, and optionally at least one memory device.

The computer-usable or computer-readable medium may be or include, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of certain embodiments of the present invention may be written in an object oriented and/or conventional procedural programming languages including, but not limited to, Java, Smalltalk, Perl, Python, Ruby, Lisp, PHP, "C", FORTRAN, or C++. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

It will be understood that functions of DLS systems described herein may be implemented by computer-readable program code modules. These program code modules may be provided to a processing module of a general purpose computer, special purpose computer, embedded processor or other programmable data processing apparatus to produce a machine, such that the program code modules, which execute via the processing module of the computer or other programmable data processing apparatus, create means for implementing the functions specified in the flowchart and/or block diagram block or blocks.

These computer program code modules may also be stored in a computer-readable memory that can direct a computer or other programmable data processing apparatus to function in a particular manner, such that the program code modules stored in the computer-readable memory produce an article of manufacture.

The computer program code modules may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

This invention can be embodied in other forms without departing from the spirit or essential attributes thereof and, accordingly, reference should be to the following claims rather than the foregoing specification as indicating the scope of the invention.

The disclosure of all references cited are incorporated in their entirety to the extent not inconsistent with the teachings herein.

What is claimed is:

1. An assay method for the detection of an analyte, said method comprising:
   providing a plurality of probes, said probes comprising a metal nanoparticles, wherein said metal nanoparticles are optionally conjugated with receptors;
   providing a plurality of aggregation inducers,
   contacting a sample solution suspected of including at least one analyte with a plurality of probes comprising a metal nanoparticles conjugated with receptors and said plurality of aggregation inducers to form assay solution, wherein said plurality of probes associates with said plurality of aggregation inducers to become aggregated nanoparticles and wherein a presence of said analyte competes with said aggregation inducers to thereby reduce aggregation of said probes;
   directing light toward said assay solution; and
   obtaining DLS data from said sample solution using dynamic light scattering, wherein said DLS data indicates a change in average particle size and/or a change in particle size distribution, and optionally, further comprising the step of
   determining a concentration of said at least one analyte if present in said assay solution from said DLS data.

2. The method of claim 1, wherein said determining step comprises obtaining the average particle size of the assay solution.

3. The method of claim 1, further comprising establishing a correlation between said relative ratio and said concentration of said analyte in said assay solution.

SEQUENCE LISTING

```
<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
taacaatccc tc                                                          12

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
atccttatca atatt                                                       15

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagggattat tgttaaatat tgataaggat                                       30
```

4. The method of claim 1, further comprising establishing a correlation between average particle size and said concentration of said analyte in said assay solution.

\* \* \* \* \*